US011241401B2

(12) United States Patent
Millet

(10) Patent No.: US 11,241,401 B2
(45) Date of Patent: *Feb. 8, 2022

(54) ENANTIOMERICALLY PURE R-BETA-HYDROXYBUTYRATE MIXED SALT-ACID COMPOSITIONS

(71) Applicant: AXCESS GLOBAL SCIENCES, LLC, Salt Lake City, UT (US)

(72) Inventor: Gary Millet, Salt Lake City, UT (US)

(73) Assignee: AXCESS GLOBAL SCIENCES, LLC, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/783,907

(22) Filed: Feb. 6, 2020

(65) Prior Publication Data
US 2021/0244690 A1 Aug. 12, 2021

(51) Int. Cl.
A61K 31/19 (2006.01)
A61K 45/06 (2006.01)
A61K 47/12 (2006.01)

(52) U.S. Cl.
CPC .............. A61K 31/19 (2013.01); A61K 45/06 (2013.01); A61K 47/12 (2013.01)

(58) Field of Classification Search
None
See application file for complete search history.

(56) References Cited

U.S. PATENT DOCUMENTS

| | | | |
|---|---|---|---|
| 2,238,149 A | 4/1941 | Aeckerle | |
| 2,976,073 A | 3/1961 | Russell et al. | |
| 4,627,808 A | 12/1986 | Hughes | |
| 4,997,976 A | 3/1991 | Brunengraber et al. | |
| 5,093,044 A | 3/1992 | Wretlind | |
| 5,116,868 A | 5/1992 | Chen et al. | |
| 5,288,512 A | 2/1994 | Seiden | |
| 5,292,774 A | 3/1994 | Hiraide et al. | |
| 5,654,266 A | 8/1997 | Chen et al. | |
| 5,700,670 A | 12/1997 | Yamagishi et al. | |
| 6,207,856 B1 | 3/2001 | Veech | |
| 6,316,038 B1 | 11/2001 | Veech | |
| 6,323,237 B1 | 11/2001 | Veech | |
| 6,380,244 B2 | 4/2002 | Martin et al. | |
| 6,613,356 B1 | 9/2003 | Vlahakos | |
| 6,706,756 B1 | 3/2004 | Fitzpatrick et al. | |
| 6,835,750 B1 | 12/2004 | Henderson | |
| 7,351,736 B2 | 4/2008 | Veech | |
| 7,807,718 B2 | 10/2010 | Hashim et al. | |
| 8,101,653 B2 | 1/2012 | Veech | |
| 8,124,589 B2 | 2/2012 | Henderson | |
| 8,426,468 B2 | 4/2013 | Henderson | |
| 8,642,654 B2 | 2/2014 | Clarke et al. | |
| 8,748,400 B2 | 6/2014 | Henderson | |
| 9,138,420 B2 | 9/2015 | D'Agostino et al. | |
| 9,211,275 B2 | 12/2015 | Clarke et al. | |
| 9,675,577 B2 | 6/2017 | D'Agostino et al. | |
| 9,717,767 B2 | 8/2017 | Carpenter et al. | |
| 9,795,580 B2 | 10/2017 | Weeber et al. | |
| 9,808,481 B2 | 11/2017 | Ritter et al. | |
| 9,957,246 B2 | 5/2018 | Stinchcomb et al. | |
| 10,022,409 B2 | 7/2018 | Carpenter et al. | |
| 10,051,880 B2 | 8/2018 | Clarke et al. | |
| 10,245,242 B1 | 4/2019 | Millet | |
| 10,245,243 B1 | 4/2019 | Millet | |
| 10,292,592 B2 | 5/2019 | Marshall et al. | |
| 10,588,876 B2 | 3/2020 | Millet | |
| 10,588,877 B2 | 3/2020 | Arnold | |
| 10,596,128 B2 | 3/2020 | Millet | |
| 10,596,129 B2 | 3/2020 | Millet | |
| 10,596,130 B2 | 3/2020 | Millet | |
| 10,596,131 B2 | 3/2020 | Millet | |
| 10,660,958 B2 | 5/2020 | Clarke | |
| 10,736,861 B2 | 8/2020 | Millet | |
| 10,925,843 B2 | 2/2021 | Millet | |

(Continued)

FOREIGN PATENT DOCUMENTS

| | | |
|---|---|---|
| CN | 1347319 | 5/2002 |
| EP | 2283834 | 2/2011 |

(Continued)

OTHER PUBLICATIONS

International Search Report and Written Opinion received for PCT Patent Application No. PCT/US2020/033159, dated Aug. 12, 2020, 9 pages.
International Search Report and Written Opinion issued in PCT/US20/16952 dated Apr. 22, 2020.
International Search Report and Written Opinion issued in PCT/US20/17555 dated May 4, 2020.
International Search Report and Written Opinion issued in PCT/US20/17556 dated May 4, 2020.
International Search Report and Written Opinion issued in PCT/US20/17552 dated May 4, 2020.

(Continued)

Primary Examiner — Jeffrey S Lundgren
Assistant Examiner — Michael J Schmitt
(74) Attorney, Agent, or Firm — Workman Nydegger

(57) ABSTRACT

A ketogenic R-beta-hydroxybutyrate mixed salt-acid composition includes enantiomerically pure R-beta-hydroxybutyric acid and one or more enantiomerically pure R-beta-hydroxybutyrate salts. The R-beta-hydroxybutyric acid is more rapidly absorbed and utilized by the body than salts or esters, enhances taste, and reduces the need to include citric acid or other edible acids. The enantiomerically pure R-beta-hydroxybutyrate salt(s) are more slowly absorbed and utilized by the body and can provide one or more electrolytes. Compositions for increasing ketone body level in a subject may contain a dietetically or pharmaceutically acceptable carrier and an R-beta-hydroxybutyrate mixed salt-acid composition. The composition contains less than 100% by molar equivalents of total enantiomerically pure R-beta-hydroxybutyrate salts and more than 0% by molar equivalents of enantiomerically pure R-beta-hydroxybutyric acid.

20 Claims, No Drawings

(56) References Cited

U.S. PATENT DOCUMENTS

| | | | |
|---|---|---|---|
| 10,973,786 | B2 | 4/2021 | Millet |
| 2001/0014696 | A1 | 8/2001 | Veech |
| 2001/0041736 | A1 | 11/2001 | Veech |
| 2003/0022937 | A1 | 1/2003 | Veech |
| 2005/0129783 | A1 | 6/2005 | McCleary |
| 2007/0179197 | A1 | 8/2007 | Henderson |
| 2008/0058416 | A1 | 3/2008 | Greenwood et al. |
| 2008/0287372 | A1 | 11/2008 | Henderson |
| 2009/0253781 | A1 | 10/2009 | Veech |
| 2010/0041751 | A1 | 2/2010 | Henderson |
| 2010/0197758 | A1 | 8/2010 | Andrews et al. |
| 2010/0298294 | A1 | 11/2010 | Clarke |
| 2012/0071548 | A1 | 3/2012 | Veech |
| 2012/0202891 | A1 | 8/2012 | Stinchcomb et al. |
| 2013/0079406 | A1 | 3/2013 | Veech |
| 2013/0337116 | A1 | 12/2013 | Petralia |
| 2015/0065571 | A1 | 3/2015 | Clarke et al. |
| 2015/0132280 | A1 | 5/2015 | Lopez et al. |
| 2016/0193173 | A1 | 7/2016 | Clarke et al. |
| 2016/0256411 | A1 | 9/2016 | Aung-Din |
| 2017/0020844 | A1 | 1/2017 | Galinski |
| 2017/0172969 | A1 | 6/2017 | D'Agostino et al. |
| 2017/0258745 | A1 | 9/2017 | Millet |
| 2017/0266148 | A1 | 9/2017 | D'Agostino et al. |
| 2017/0290792 | A1 | 10/2017 | Cavaleri |
| 2017/0296501 | A1* | 10/2017 | Lowery ............... A61K 47/06 |
| 2017/0298339 | A1 | 10/2017 | Hanson et al. |
| 2017/0304564 | A1 | 10/2017 | DeHaan et al. |
| 2018/0021274 | A1 | 1/2018 | Arnold |
| 2018/0055797 | A1* | 3/2018 | LLosa ................. A61K 31/19 |
| 2018/0057846 | A1* | 3/2018 | LLosa ................... C12P 7/26 |
| 2018/0195096 | A1 | 7/2018 | Veech et al. |
| 2019/0099394 | A1 | 4/2019 | D'Agostino et al. |
| 2019/0167613 | A1 | 6/2019 | Millet |
| 2019/0183820 | A1 | 6/2019 | Millet |
| 2019/0313682 | A1 | 10/2019 | Nagel |
| 2020/0078973 | A1 | 3/2020 | Valeze et al. |
| 2020/0140371 | A1 | 5/2020 | Verdin et al. |

FOREIGN PATENT DOCUMENTS

| | | |
|---|---|---|
| EP | 3094321 | 5/2019 |
| EP | 2976073 | 8/2019 |
| JP | 11060434 | 3/1999 |
| JP | 2002521330 | 7/2002 |
| JP | 2020-502652 A | 1/2020 |
| JP | 2020-527583 A | 9/2020 |
| JP | 2021-504476 A | 2/2021 |
| JP | 2021-506294 A | 2/2021 |
| RU | 2345546 | 4/2008 |
| WO | WO8703808 | 7/1987 |
| WO | WO 98/41200 | 9/1998 |
| WO | WO 03/070823 | 8/2003 |
| WO | WO2005107724 | 11/2005 |
| WO | WO2007115282 | 10/2007 |
| WO | WO2008005818 | 1/2008 |
| WO | WO 2008/021394 | 2/2008 |
| WO | WO 2008/024408 | 2/2008 |
| WO | WO2011101171 | 8/2011 |
| WO | 2013/150153 A1 | 10/2013 |
| WO | WO 2014153416 | 9/2014 |
| WO | 2015/071811 A1 | 5/2015 |
| WO | 2015/156865 A1 | 10/2015 |
| WO | WO2016123229 | 8/2016 |
| WO | WO 2017/208217 | 12/2017 |
| WO | WO 2018/089863 | 5/2018 |
| WO | WO2019018683 | 1/2019 |
| WO | 2019/237152 A1 | 12/2019 |

OTHER PUBLICATIONS

Veech, et al., "Ketone Bodies Mimic the Life Span Extending Properties of Caloric Restriction", IUBMB Life Feb. 8, 2017.
Murray, Andrew J., et al. "Novel ketone diet enhances physical and cognitive performance", The FASEB Journal, Vo. Dec. 30, 2016.
Hashim, Sami A., et al., "Ketone body therapy: from the ketogenic diet to the oral administration of ketone ester", Journal of Lipid Research, vol. 55, 2014.
Nova Max Plus Glucose and Ketone Testing with One Monitor. Downloaded Apr. 1, 2015. http://www.novacares.com/nova-max-plus/.
Serum Ketones Test. MedlinePlus Medical Encyclopedia. Downloaded Apr. 1, 2015. http://www.nlm.nih.gov/medlineplus/ency/article/003498.htm.
It Really is in Your Blood: Glucose to Ketone Ratios. Greymadder, Sep. 15, 2014. Downloaded Apr. 1, 2015. http://greymadder.net/2014/09/15/it-really-is-in-your-blood-glucose-to-ketone-ratios/.
A New Toy Measuring Blood Ketones. Diet Doctor, Aug. 21, 2012. Dowloaded Apr. 1, 2015. http://www.dietdoctor.com/a-new-toy-measuring-blood-ketoones.
Precision Xtra vs. NovaMax Plus: Ketone Meter Evaluation. Jimmy Moore's Livin' La Vida Low Carb Blog. Downloaded Apr. 1, 2015. http://livinlavidalowcarb.com/blog/precision-xtra-vs-novamax-plus-ketone-meter-evaluation/15918.
Kirsch, Jr et al. "Butanediol Induced Ketosis Increases Tolerance to Hypoxia in the Mouse." Stroke. 1980. Vol. 11, No. 5, pp. 506-513.
Kossoff, Eric H. et al. "Optimal Clinical Management of Children Receiving the Ketogenic Diet Recommendations of the International Ketogenic Diet Study Group." Epilepsia, Feb. 2009;50(2):304-17. Epub Sep. 23, 2008.
Henderson, Samuel T. "Ketone Bodies as a Therapeutic for Alzheimer's Disease." Neurotherapeutics. Jul. 2008;5 3 3):470-80.
Veech, Richard L. "The Therapeutic Implications of Ketone Bodies: The Effects of Ketone Bodies in Pathological Conditions: Ketosis, Ketogenic Diet, Redox States, Insulin Resistance, and Mitochondrial Metabolism." Prostaglandins Leukot Essent Fatty Acids. Mar. 2004;70(3):309-19.
Krotkiewski, M. "Value of VLCD Supplementation with Medium Chain Triglycerides." I'nt J Obes Relat Metab Disord. Sep. 2001;2 5(9):1 39300.
PCT International Search Report and Written Opinion issued by the International Searching Authority dated Jul. 15, 2014 or International Patent Application No. PCT/US2014/031237.
Arnold, Instant Ketosis?, (2013), Aug. 4, 2013 (retrieved on Apr. 21, 2017), p. 1-3. Retrieved from the internet; URL: < http://patrickarnoldblog.com/instant-ketosis/. (Year: 2013).
Parker, Steve, "Ketogenic Mediterranean Diet: Version 2.3," Nov. 23, 2010, pp. 1-3. (Year: 2010).
Sajewicz et al. in Journal of Liquid Chromatography & Related Technologies, 33:1047-1057 (2010) (Year: 2010).
Shigeno et al. in Biosci. Biotech. Biochem., 56(2), 320-323 (1992) (Year: 1992).
Optical Purity and Enantiomeric Excess at https://www.masterorganicchemistry.com/2017/02/24/optical-purity-and-enantiomeric-excess/. (Retrieved from the internet Nov. 6, 2018) (Year: 2018).
Tisdale, "Reduction of weight loss and tumour size in a cachexia model by a high fat diet", British Journal of Cancer, Jul. 1987, vol. 56, p. 39-43.
Tanaka, J., et al., "Significance of Blood Ketone Body Ration as an indicator of Hepatic Cellular Energy Status in Jaundiced Rabbits", Gastroenterology, 1979, vol. 76, No. 4, pp. 691-696.
International Search Report cited in PCT/US19/27214 dated Jun. 25, 2019.
Written Opinion cited in PCT/US19/27214 dated Jun. 25, 2019.
International Search Report cited in PCT/US18/62093 dated Feb. 1, 2019.
International Search Report cited in PCT/US18/62096 dated Feb. 11, 2019.
Pubchem, "Acetoacetic acid" Electronic Resource https://pubchem.ncbi.nim.nih.gov/compound/Acetoacetic-acid, Retrieved on Sep. 3, 2019.
Arendash et al. "Caffeine and Coffee as Therapeutics Against Alzheimer's Disease", Journal of Alzheimer's Disease 20, 2010, S117-S126.
Kesl, et al., "Effects of exogenous ketone supplementation on blood ketone, glucose, triglyceride, and lipoprotein levels in Sprague-Dawley rats", Nutrition & Metabolism (2016).

(56) References Cited

OTHER PUBLICATIONS

Extended European Search Report issued in PCT/US2017021886 dated Oct. 17, 2019.
International Search Report and Written Opinion issued in PCT/US19/48364 dated Nov. 15, 2019.
International Search Report and Written Opinion issued in PCT/US19/48357 dated Nov. 18, 2019.
Karppanen, H., et al., "Why and how to implement sodium, potassium, calcium, and magnesium changes in food items and diets?"
U.S. Appl. No. 14/455,385, filed Jan. 2, 2015, Office Action.
U.S. Appl. No. 14/860,092, filed Mar. 9, 2016, Office Action.
U.S. Appl. No. 14/860,092, filed Oct. 17, 2016, Office Action.
U.S. Appl. No. 15/610,668, filed Jul. 25, 2018, Office Action.
U.S. Appl. No. 15/454,157, filed Jan. 11, 2018, Office Action.
U.S. Appl. No. 15/454,157, filed Jun. 13, 2018, Office Action.
U.S. Appl. No. 15/936,820, filed Nov. 14, 2018, Office Action.
U.S. Appl. No. 15/936,849, filed Nov. 14, 2018, Office Action.
U.S. Appl. No. 15/454,157, filed Feb. 26, 2019, Notice of Allowance.
U.S. Appl. No. 15/936,849, filed Jan. 24, 2019, Notice of Allowance.
U.S. Appl. No. 16/272,328, filed Jul. 29, 2019, Office Action.
U.S. Appl. No. 16/272,359, filed Feb. 11, 2019, Notice of Allowance.
U.S. Appl. No. 16/381,202, filed Oct. 22, 2019, Office Action.
U.S. Appl. No. 16/224,485, filed Nov. 27, 2019, Notice of Allowance.
U.S. Appl. No. 16/224,408, filed Nov. 27, 2019, Notice of Allowance.
U.S. Appl. No. 16/272,145, filed Jan. 10, 2020, Office Action.
U.S. Appl. No. 16/409,501, filed Jan. 14, 2020, Notice of Allowance.
Clarke, et al., Kinetics, safety and tolerability of (R)-3-hydroxybutyl (R)-3-hydroxybutyrate in healthy adult subjects. Regul Toxicol Pharmacol. Aug. 2012;63(3):401-8.
First Examination Report for New Zealand Patent Application No. 711433 issued by the New Zealand Intellectual Property Office dated Mar. 10, 2016.
First Office Action issued by the Chinese State Intellectual Property Office dated Nov. 4, 2016 for corresponding Chinese Patent Application No. 201480016818.0.
Karppanen et al., J. Human Hypertension (2005), vol. 19, pp. S10-S19. (Year: 2005).
Roeder, Lois M., et al. The Effects of Ketone Bodies, Bicarbonate, and Calcium on Hepatic Mitochondrial Ketogenesis Archives of Biochemistry and Biophysics, vol. 217, No. 2, Sep. pp. 460-467, 1982.
Vorgerd, M. and J. Zange. Treatment of glycogenosys type V (McArdle disease) with creatine and ketogenic diet with clinical scores and with 31P-MRS on working leg muscle. Acta Myologica, 2007; XXVI; pp. 61-63.
Amazon, "Perfect Keto Perform Pre Workout Powder—Burn Fat for Fuel Energy Supplement Drink Mix for Men and Women—Keto Friendly with Ketone Salts, BCAA, Nitric Oxide & MCT", Sep. 25, 2017 entire document especially p. 1 Retrieved from https://www.amazon.com/Perfect-Keto-Perform-PreworkoutSupplement/dp/B0751379Q9/ref=sr_1_9?dchild=1&keywords=ketone+pre+workout&qid=1597938465&sr=8-9.
Dietary Guidelines Recommendations at https://health.gov/our-work/food-nutrition/2015-2020-dietary-guidelines/guidelines/ appendix-7/ (2010) (retrieved from the internet Oct. 20, 2020) (Year: 2010).
Holtzman et al., "Role of adenosine receptors in caffeine tolerance", J. Pharmacol. Exp. Ther., 1991 ;256(1 ):62-68.

International Search Report and Written Opinion received for PCT Patent Application No. PCT/US20/37289, dated Sep. 30, 2020, 8 pages.
Non-Final Office Action received for U.S. Appl. No. 16/381,202, dated Aug. 11, 2020, 8 pages.
Non-Final Office Action received for U.S. Appl. No. 16/720,211, dated Oct. 28, 2020, 14 pages.
Non-Final Rejection dated Sep. 9, 2020 for U.S. Appl. No. 16/783,956.
Notice of Allowance received for U.S. Appl. No. 16/381,202, dated Nov. 10, 2020, 8 pages.
Office Action cited in U.S. Appl. No. 16/720,211 dated Oct. 28, 2020.
Office Action cited in U.S. Appl. No. 16/996,509 dated Oct. 26, 2020.
Parker, Steve, "Ketogenic Mediterraanean Diet: Version 2.3," Nov. 23, 2010, pp. 1-3. (Year: 2010).
Requirement for Restriction/Election received for U.S. Appl. No. 16/551,570, dated Sep. 28, 2020, 6 pages.
Vandenberghe et al. in Can. J. Physiol. Pharmacol. 95:455-458 (2017) (Published at www.nrcresearchpress com/cjpp on Nov. 25, 2016). (Year: 2016).
A New Toy Measuring Blood Ketones Diet Doctor, Aug. 21, 2012. Downloaded Apr. 1, 2015. http://www.dietdoctor.com/a-new-toy-measuring-blood-ketoones.
Bastin et al., "Salt Slection and Optimisation Procedures for Pharmaceutical New Chemical Entities", American Chemical Society and The Royal Society of Chemistry, vol. 4, No. 5, 2000, pp. 427-435.
Cresci, G. et al., Lactobacillus GG and Tributyrin Supplementation Reduce Antibiotic-Induced Intestinal Injury, 2013, Journal of Parenteral and Enteral Nutrition, 37(6), 1-20 (Year: 2013).
Dolson, Laura. How to Test Your Blood for Ketones. Downloaded Apr. 1, 2015. http://lowcarbdiets.about.eom/od/KetogenicDiets/a/How-to-Test-Blood-For Ketones.htm.
Haywood A, Glass BD. Pharmaceutical excipients—where do we begin? Australian Prescriber. 2011; 34:112-114.
Ichim, T. et al., Experimental support for the effects of a probiotic/digestive enzyme supplement on serum cholesterol concentrations and the intestinal microbiome, 2016, Journal of Translational Medicine, 14(184), 1-9 (Year: 2016).
International Preliminary Reporton Patentability received for PCT Patent Application No. PCT/US2019/048364, dated Mar. 11, 2021, 7 pages.
International Search Report and Written Opinion received for PCT Patent Application No. PCT/US21/17078, dated Apr. 23, 2021, 9 pages.
Malo, M. S. et al., Intestinal alkaline phosphatase preserves the normal homeostasis of gut microbiota, 2010, Gut, 59, 1476-1484 (Year: 2010).
Robson et al. Expert Opin. Drug Saf. (2011), vol. 10, pp. 675-685 (Year: 2011).
Acetoacetate, Acetone, and Dibenzylamine (A Contaminant in L-(+)-Beta-Hydroxybutyrate) Exhibit Direct Anticonvulsant Actions in Vivo, Epilepsia, Raven Press Ltd, New York, US, vol. 43, No. 4, Apr. 1, 2002 (Apr. 1, 2002), pp. 358-361.
Haces M L et al.: "Antioxidant capacity contributes to protection of ketone bodies against oxidative damage induced during hypoglycemic conditions", Experimental Neurology, Elsevier, Amsterdam, NL, vol. 211, No. 1, May 1, 2008 (May 1, 2008), pp. 85-96.
Stubbs et al., "On the Metabolism of Exogenous Ketones in Humans", frontiers in Physiology, vol. 8, 2017, 13 pages.
Tsai et al., "Stereoselective effects of 3-hydroxybutyrate on glucose utilization of rat cardiomyocytes" life Sciences 78(2006) pp. 1385-1391.

* cited by examiner

ENANTIOMERICALLY PURE R-BETA-HYDROXYBUTYRATE MIXED SALT-ACID COMPOSITIONS

CROSS-REFERENCE TO RELATED APPLICATIONS

None.

BACKGROUND

1. Field of the Invention

Disclosed herein are R-beta-hydroxybutyrate compounds, salts, acids and compositions methods of use.

2. Related Technology

In periods of fasting, extreme exercise, and/or low carbohydrate consumption, glucose and glycogen stores in the body are rapidly used and can become quickly depleted. Failure to replenish glucose stores as they become depleted causes the body to metabolically shift to the creation and use of ketone bodies for energy ("ketosis"). Ketone bodies can be used by cells of the body as a fuel to satisfy the body's energy needs, including the brain and heart. During prolonged fasting, for example, blood ketone levels can increase to 2-3 mmol/L or more. It is conventionally understood that when blood ketones rise above 0.5 mmol/L, the heart, brain and peripheral tissues are using ketone bodies (e.g., beta-hydroxybutyrate and acetoacetate) as the primary fuel source. This condition is referred to as ketosis. At blood levels between 1.0 mmol/L and 3.0 mmol/L the condition is called "nutritional ketosis."

Upon transitioning into ketosis, or in other words, during ketogenic metabolism in the liver, the body uses dietary and bodily fats as a primary energy source. Consequently, once in ketosis, one can induce loss of body fat by controlling dietary fat intake and maintaining low carbohydrate intake and blood level to sustain ketosis.

During ketosis, the body is in ketogenesis and essentially burning fat for its primary fuel. The body cleaves fats into fatty acids and glycerol and transforms fatty acids into acetyl CoA molecules, which are then eventually transformed through ketogenesis into the water-soluble ketone bodies beta-hydroxybutyrate (i.e., "β-hydroxybutyrate" or "BHB"), acetoacetate (also known as acetylacetonate), and acetone in the liver. Beta-hydroxybutyrate and acetoacetate are the primary ketone bodies used by the body for energy while acetone is removed and expelled as a byproduct of ketogenesis.

The metabolism of ketone bodies is associated with several beneficial effects, including anticonvulsant effects, enhanced brain metabolism, neuroprotection, muscle sparing properties, and improved cognitive and physical performance. Science-based improvements in efficiency of cellular metabolism, managed through ketone supplementation, can have beneficial impacts on physical, cognitive health, and psychological health, and a long-term impact on health with respect to common avoidable diseases such as obesity, cardiovascular disease, neurodegenerative diseases, diabetes, and cancer.

Despite the many health advantages of pursuing a ketogenic diet or lifestyle and maintaining a state of nutritional ketosis, there remain significant barriers to pursuing and maintaining a ketogenic state. One of these barriers is the difficulty of transitioning into a ketogenic state. The fastest endogenous way to entering ketosis through depleting glucose stores in the body is by fasting combined with exercise. This is physically and emotionally demanding and is extremely challenging even for the most motivated and disciplined.

Additionally, the transition into ketosis is often accompanied by hypoglycemia, which can cause lethargy and light-headedness in many, resulting in an uncomfortable physiological and mental state commonly referred to as the "low-carb flu." In addition, many people experience a down regulation in their metabolism as the body naturally goes into an "energy-saving" mode. Some suggest that these transitory symptoms may last as long as two to three weeks. During this transition period, if a subject consumes a meal or snack containing carbohydrates above the restrictive amount, there is an immediate termination of ketogenisis, exiting the body from its state of ketosis, as the body shifts back to glucose utilization for its primary fuel and the transition into ketosis must begin anew.

If a subject is successful in establishing ketosis, the act of sustaining ketosis is likewise difficult, if not more difficult, due to the need to maintain a rigid dietary ratio of carbohydrates and protein to fats. It is further complicated by the disruption of normal electrolyte balances that often occurs when transitioning into and maintaining a ketogenic state. The depletion and lowering of glycogen stores in the liver and muscles lessens the ability of the body to retain water, leading to more frequent urination, and accordingly, a greater loss of electrolytes. Further, the drop in insulin levels caused by ketosis effects the rate at which certain electrolytes are extracted by the kidneys, additionally lowering electrolyte levels in the body. Negative effects of electrolyte imbalance include muscle aches, spasms, twitches and weakness, restlessness, anxiety, frequent headaches, feeling very thirsty, insomnia, fever, heart palpitations or irregular heartbeats, digestive issues such as cramps, constipation or diarrhea, confusion and trouble concentrating, bone disorders, joint pain, blood pressure changes, changes in appetite or body weight, fatigue (including chronic fatigue syndrome), numbness in joints, and dizziness, especially when standing up suddenly.

Some compositions used to promote ketosis in a mammal include a racemic mixture of beta-hydroxybutyrate (RS-beta-hydroxybutyrate or DL-beta-hydroxybutyrate). US 2017/0296501 and EP 1755743 disclose the use of R-beta-hydroxybutyrate salts, esters and oligomers. U.S. Pat. No. 8,642,654 discloses the use of the beta-hydroxybutyrate ester: (3R)-hydroxybutyl (3R)-hydroxybutyrate.

BRIEF SUMMARY

Disclosed herein are enantiomerically pure R-beta-hydroxybutyrate mixed salt-acid compositions and methods of use. The R-beta-hydroxybutyrate mixed salt-acid compositions can be used for controlling ketone body levels in a subject, including promoting and/or sustaining ketosis in a subject over an extended period of time.

The R-beta-hydroxybutyrate enantiomer is endogenously produced by a mammal during ketosis. Therefore, enantiomerically pure R-beta-hydroxybutyrate administered to a subject can be immediately utilized by the body, such as for producing energy (e.g., as an alternative energy source to glucose).

R-beta-hydroxybutyrate mixed salt-acid compositions include a quantity of free R-beta-hydroxybutyric acid combined with one or more salts of R-beta-hydroxybutyrate. This provides an optimized or acceptable electrolyte load coupled with rapid absorption, particularly when a relatively high amount of the composition is administered to a subject. This provides a greater and/or faster ketogenic effect compared to R-beta-hydroxybutyrate salts and/or esters administered without free R-beta-hydroxybutyric acid.

Combining R-beta-hydroxybutyric acid with one or more R-beta-hydroxybutyrate salts is highly beneficial because it reduces electrolyte load, increases absorption rate, improves taste, facilitates easier formulation, and reduces the need to add citric acid or other edible acids to obtain a composition having neutral or acidic pH.

In some embodiments, the compositions disclosed herein can be used in a method for increasing ketone body level in a subject, including promoting and/or sustaining ketosis in a subject, comprising administering to a subject in need thereof a nutritionally or pharmaceutically effective amount of one or more compositions disclosed herein. Examples of beneficial effects of increased ketone body level in a subject include one or more of appetite suppression, weight loss, fat loss, reduced blood glucose level, improved mental alertness, increased physical energy, improved cognitive function, reduction in traumatic brain injury, reduction in effect of diabetes, improvement of neurological disorder, reduction of cancer, reduction of inflammation, anti-aging, antiglycation, reduction in epileptic seizer, improved mood, increased strength, increased muscle mass, or improved body composition.

In some embodiments, the composition may include a nutritionally or pharmaceutically acceptable carrier.

Additional features and advantages will be set forth in part in the description that follows, and in part will be obvious from the description, or may be learned by practice of the embodiments disclosed herein. It is to be understood that both the foregoing brief summary and the following detailed description are exemplary and explanatory only and are not restrictive of the embodiments disclosed herein or as claimed.

DETAILED DESCRIPTION

I. Definitions

The compound "beta-hydroxybutyrate," also known as β-hydroxybutyrate, 3-hydroxybutyrate, βHB, or BHB, is the deprotonated form of beta-hydroxybutyric acid, which is a hydroxycarboxylic acid having the general formula $CH_3CH_2OHCH_2COOH$. The deprotonated form present at typical biological pH levels is $CH_3CH_2OHCH_2COO^-$. The general chemical structure shown below represents beta-hydroxybutyrate compounds that may be utilized in the disclosed compositions:

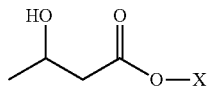

where,
X can be hydrogen, metal ion, amino cation such as from an amino acid, alkyl, alkenyl, aryl, or acyl.

When X is a hydrogen, the compound is beta-hydroxybutyric acid. When X is a metal ion or an amino cation, the compounds is a beta-hydroxybutyrate salt. When X is alkyl, alkenyl, aryl, or acyl, the compounds is a beta-hydroxybu-tyrate ester. The foregoing compounds can be in any desired physical form, such as crystalline, powder, solid, liquid, solution, suspension, or gel.

The term "enantiomerically pure R-beta-hydroxybutyrate" means that it contains only the endogenously produced R-enantiomer of beta-hydroxybutyrate and is not combined with S-beta-hydroxybutyrate, which is often produced as a byproduct when industrially producing exogenous R-beta-hydroxybutyrate. Because S-beta-hydroxybutyrate is not produced by the body, it is excluded from the disclosed compositions.

The term "R-beta-hydroxybutyrate mixed salt-acid composition" means a composition that includes one or more salts of R-beta-hydroxybutyrate and free R-beta-hydroxybutyric acid.

The term "R-beta-hydroxybutyrate salt" does not mean or imply any particular physical state, such as a crystalline, powder, other solid form, dissolved in water to form a liquid solution, dispersed in a liquid to form a suspension, or gel. A salt can be formed in solution by neutralizing beta-hydroxybutyric acid with a strong or weak base, such as an alkali or alkaline earth metal hydroxide, carbonate, or bicarbonate, basic amino acid, and the like.

The term "free R-beta-hydroxybutyric acid" means the sum of non-deprotonated and deprotonated R-beta-hydroxybutyric acid molecules. A deprotonated R-beta-hydroxybutyric acid molecule generally means a molecule that has released a proton to form a hydronium ion ($H_3O+$) and an R-beta-hydroxybutyrate anion (e.g., dissolved in water).

Free R-beta-hydroxybutyric acid molecules are typically not deprotonated to any significant degree when contained in a R-beta-hydroxybutyrate mixed salt-acid composition in dry powder or other solid form. In such cases, the fractional amount of free R-beta-hydroxybutyric acid in a R-beta-hydroxybutyrate mixed salt-acid composition on a weight basis is the weight of free R-beta-hydroxybutyric acid divided by the combined weight of free R-beta-hydroxybutyric acid and R-beta-hydroxybutyrate salt(s). On a molar basis, the fractional amount of free R-beta-hydroxybutyric acid in an R-beta-hydroxybutyrate mixed salt-acid composition are the molar equivalents of free R-beta-hydroxybutyric acid divided by the sum of molar equivalents of free R-beta-hydroxybutyric acid and R-beta-hydroxybutyrate anions provided by the R-beta-hydroxybutyrate salt(s).

When dissolved in water, a portion of the R-beta-hydroxybutyric acid will typically dissociate into R-beta-hydroxybutyrate anions and hydronium ions ($H_3O+$). As a result, R-beta-hydroxybutyric acid molecules can exchange protons and cations with dissolved R-beta-hydroxybutyrate salts. For purposes of defining the relative amounts of R-beta-hydroxybutyric acid and R-beta-hydroxybutyrate salt(s) in a R-beta-hydroxybutyrate mixed salt-acid composition, dissociation of R-beta-hydroxybutyric acid molecules and the exchange of protons and cations is not understood as changing the molar ratio of free R-beta-hydroxybutyric acid relative to R-beta-hydroxybutyrate anions from the R-beta-hydroxybutyrate salt(s). The total quantity of free R-beta-hydroxybutyric acid molecules in solution is the sum of dissolved R-beta-hydroxybutyric acid molecules that are not deprotonated and R-beta-hydroxybutyrate anions formed by deprotonation of R-beta-hydroxybutyric acid molecules.

Stated another way, the total molar equivalents of R-beta-hydroxybutyric acid in solution, whether or not deprotonated, is understood to be the difference between (i) the sum of molar equivalents of non-deprotonated R-beta-hydroxybutyric acid molecules and total molar equivalents of R-beta-hydroxybutyrate anions in solution (from all sources) and (ii) the total molar equivalents of cationic charge provided by cations from the R-beta-hydroxybutyrate salt compounds (which equals the total molar equivalents of R-beta-hydroxybutyrate anions provided by the R-beta-hydroxybutyrate salt(s)). Alkali metal cations such as sodium and potassium provide 1 mole of cationic charge per mole of metal cations. Alkaline earth metal cations such as magnesium and calcium, on the other hand, provide 2 moles of cationic charge per mole of metal cations. 1 mole of deprotonated R-beta-hydroxybutyric acid molecules provide 1 mole of anionic charge and one mole of cationic charge.

In view of the foregoing, the molar fraction of R-beta-hydroxybutyric acid in solution in relation to total moles of R-beta-hydroxybutyrate molecules from the R-beta-hydroxybutyrate mixed salt-acid composition in solution is [(i)−(ii)÷(i)], and the molar fraction of R-beta-hydroxybutyrate molecules from the R-beta-hydroxybutyrate salt(s)) in solution is [(ii)÷(i)]. Multiplying the molar fraction of each by 100 gives the percentage of each in solution.

By way of example, if 100 molar equivalents of R-beta-hydroxybutyrate mixed salt-acid composition in a dry powdered state contained 5% of free non-deprotonated R-beta-hydroxybutyric acid and 95% R-beta-hydroxybutyrate salt(s) on a molar basis, there would be essentially 5 molar equivalents of R-beta-hydroxybutyric acid molecules and 95 molar equivalents of R-beta-hydroxybutyrate anions. When there is sufficient water to dissolve the R-beta-hydroxybutyrate salt(s), and if a portion of the R-beta-hydroxybutyric acid molecules were deprotonated, the molar equivalents of non-deprotonated R-beta-hydroxybutyric acid would be less than 5 and the molar equivalents of R-beta-hydroxybutyrate anions would be greater than 95. The extent of deprotonation of R-beta-hydroxybutyric acid in solution is related to solution pH.

As used herein, a "ketogenic composition" is formulated to increase ketone body level in a subject, including inducing and/or sustaining a state of elevated ketone bodies at a desired level, such as ketosis, in a subject to which it is administered.

As used herein, "subject" or "patient" refers to members of the animal kingdom, including mammals, such as but not limited to, humans and other primates; rodents, fish, reptiles, and birds. The subject may be any animal requiring therapy, treatment, or prophylaxis, or any animal suspected of requiring therapy, treatment, or prophylaxis. Prophylaxis means that regiment is undertaken to prevent a possible occurrence, such as where a high glucose or diabetes is identified. "Patient" and "subject" are used interchangeably herein.

"Ketosis" as used herein refers to a subject having blood ketone levels within the range of about 0.5 mmol/L and about 16 mmol/L in a subject. Ketosis may improve mitochondrial function, decrease reactive oxygen species production, reduce inflammation and increase the activity of neurotrophic factors. "Keto-adaptation" as used herein refers to prolonged nutritional ketosis (>1 week) to achieve a sustained nonpathological "mild ketosis" or "therapeutic ketosis."

In some cases, "elevated ketone body level" may not mean that a subject is in a state of "clinical ketosis" but nevertheless has an elevated supply of ketones for producing energy and/or for carrying out other beneficial effects of ketone bodies. For example, a subject that is "ketone adapted" may not necessarily have elevated blood serum levels of ketone bodies but rather is able to utilize available ketone bodies more rapidly compared to a subject that is not "ketone adapted." In such case, "elevated ketone body level" can refer to the total quantity and/or rate of ketone bodies being utilized by the subject rather than blood plasma levels per se.

The term "administration" or "administering" is used herein to describe the process in which the disclosed compositions are delivered to a subject. The composition may be administered in various ways including oral, intragastric, and parenteral (referring to intravenous and intra-arterial and other appropriate parenteral routes), among others.

II. R-Beta-Hydroxybutyrate Mixed Salt-Acid Compositions

The R-beta-hydroxybutyrate mixed salt-acid compositions disclosed herein contain one or more enantiomerically pure R-beta-hydroxybutyrate salts and enantiomerically pure R-beta-hydroxybutyric acid. Providing a quantity of R-beta-hydroxybutyric acid is beneficial because of its much quicker absorption response time compared to salt forms of R-beta-hydroxybutyrate. Moreover, even though free R-beta-hydroxybutyric acid is ordinarily a liquid that forms an acidic solution of low pH when mixed in water and has an unpalatable taste, when combined with salt forms of R-beta-hydroxybutyrate and where the amount of beta-hydroxybutyric acid is relatively small relative to the salt form(s), the composition can still form a solid, powder or other form typical of salt forms. In such case, the combined salt and acid forms of R-BHB have acceptable pH and taste. R-beta-hydroxybutyrate mixed salt-acid compositions have substantial advantages over pure R-beta-hydroxybutyrate salts and esters, including increased absorption rate, increased bioavailability, lower electrolyte load, ease of manufacture, significantly improved taste, and reduced need for citric acid or other edible acids to obtain a composition with neutral or acidic pH.

In some embodiments, the R-beta-hydroxybutyrate mixed salt-acid composition contains less than 100% of one or more enantiomerically pure R-beta-hydroxybutyrate salts and greater than 0% of free enantiomerically pure R-beta-hydroxybutyric acid. R-beta-hydroxybutyrate mixed salt-acid compositions may contain, on a molar basis, up to 99.9%, 99.8%, 99.7%, 99.6%, 99.5%, 99.4%, 99.3%, 99.2%, 99.1%, 99%, 98.8%, 98.65%, 98.5%, 98.35%, 98.2%, 98%, 97.75%, 97.5%, 97.25%, or 97%, and at least 75%, 80%, 85%, 90%, 92%, 94%, 95%, 96%, or 97%, of one or more enantiomerically pure R-beta-hydroxybutyrate salts and at least 0.1%, 0.2%, 0.3%, 0.4%, 0.5%, 0.6%, 0.7%, 0.8%, 0.9%, 1%, 1.2%, 1.35%, 1.5%, 1.65%, 1.8%, 2%, 2.25%, 2.5%, 2.75%, or 3%, and less than 25%, 20%, 15%, 10%, 8%, 6%, 5%, 4%, or 3%, of free enantiomerically pure R-beta-hydroxybutyric acid. The foregoing percentages are expressed on a molar basis (e.g., moles of free R-beta-hydroxybutyric acid relative to total moles of R-beta-hydroxybutyrate compounds in both salt and acid forms).

Whether beta-hydroxybutyrate is the S- or R-enantiomer depends on the tetrahedral orientation of the hydroxy (or oxy group in the case of an ester) on the 3-carbon (beta-carbon) in relationship to the planar carboxyl group. In the present disclosed, the S-enantiomer forms are excluded. R-beta-hydroxybutyrate mixed salt-acid compositions contain 100% by enantiomeric equivalents of combined R-beta-hydroxybutyrate salt(s) and R-beta-hydroxybutyric acid and 0% by enantiomeric equivalents of S-beta-hydroxybutyrate salt(s) and S-beta-hydroxybutyric acid.

R-beta-hydroxybutyrate is the endogenous form produced by the body from fats and can be utilized by a subject as a fuel source during instances of low glucose levels or when a subject's body is supplemented with a usable form of R-beta-hydroxybutyrate. R-beta-hydroxybutyrate is commonly referred to as a "ketone body".

The R-beta-hydroxybutyrate mixed salt-acid compositions can be used, for example, to produce one or more desired effects in the subject, including but not limited to, appetite suppression, weight loss, fat loss, reduced blood glucose level, improved mental alertness, increased physical energy, improved cognitive function, reduction in traumatic brain injury, reduction in effect of diabetes, improvement of neurological disorder, reduction of cancer, reduction of inflammation, anti-aging, antiglycation, reduction in epileptic seizer, improved mood, increased strength, increased muscle mass, or improved body composition.

In some embodiments, the R-beta-hydroxybutyrate mixed salt-acid compositions may include or be combined with a carrier, such as a dietetically or pharmaceutically acceptable carrier. Examples carrier or forms of the composition include powders, liquids, tablets, capsules, food products, food additives, beverages, vitamin fortified beverages, beverage additives, candies, suckers, pastilles, food supplements, sprays, injectables, and suppositories.

In some embodiments, the R-beta-hydroxybutyrate mixed salt-acid compositions can include one or more salts of alkali metals, alkaline earth metals, transition metals, amino acids, or metabolites of amino acids. Examples include lithium salts, sodium salts, potassium salts, magnesium salts, calcium salts, zinc salts, iron salts (as iron II and/or iron III), chromium salts, manganese salts, cobalt salts, copper salts, molybdenum salts, selenium salts, arginine salts, lysine salts, leucine salts, isoleucine salts, histidine salts, ornithine salts, citrulline salts, glutamine salts, and creatine salts.

In some embodiments, the composition may further include or be combined with at least one short chain fatty acid, or a mono-, di- or triglyceride of the at least one short chain fatty acid, wherein the short chain fatty acid has less than 6 carbons. Example short chain fatty acids include acetic acid, propionic acid, butyric acid, isobutyric acid, valeric acid, and isovaleric acid. An example short chain triglyceride is tributyrin. Such molecules can provide protection to the gut and improve microbiome health.

The composition may include or be combined with at least one medium chain fatty acid, or a mono-, di- or triglyceride of the at least one medium chain fatty acid, wherein the medium chain fatty acid has from 6 to 12 carbons, preferably from 8 to 10 carbons. Example medium chain fatty acids are caproic acid, caprylic acid, capric acid, and lauric acid. Medium chain triglycerides (MCT), medium chain fatty acids, and mono- and di-glycerides are ketone body precursors that can provide an additional source for the production of ketone bodies independent of R-beta-hydroxybutyrate.

The composition may include or be combined with at least one long chain fatty acid, or a mono-, di- or triglyceride of the at least one long chain fatty acid, having more than 12 carbons. Examples of long-chain fatty acids include myristic acid, palmitic acid, stearic acid, arachidic acid, behenic acid, lignoceric acid, cerotic acid, omega-3 fatty acids, omega-6 fatty acids, omega-7 fatty acids, and omega-9 fatty acids.

Examples and sources of medium chain fatty acids, or esters thereof, such as a medium chain triglyceride, include coconut oil, coconut milk powder, fractionated coconut oil, palm oil, palm kernel oil, caprylic acid, capric acid, isolated medium chain fatty acids, such as isolated hexanoic acid, isolated octanoic acid, isolated decanoic acid, medium chain triglycerides either purified or in natural form such as coconut oil, and ester derivatives of the medium chain fatty acids ethoxylated triglyceride, enone triglyceride derivatives, aldehyde triglyceride derivatives, monoglyceride derivatives, diglyceride derivatives, and triglyceride derivatives, and salts of the medium chain triglycerides. Ester derivatives optionally include alkyl ester derivatives, such as methyl, ethyl, propyl, butyl, hexyl, etc.

The administration of R-beta-hydroxybutyrate mixed salt-acid compositions results in elevation of blood levels of ketone bodies, thereby exploiting the metabolic and physiological advantages of ketosis. Raising the levels of ketone bodies in the blood provides a subject with greater flexibility in diet options as compared to methods that aim to induce and sustain ketosis based on diet alone (e.g., based on fasting and/or limited carbohydrate intake). For example, a subject that has been administered an appropriate amount of R-beta-hydroxybutyrate mixed salt-acid composition will be able to eat an occasional carbohydrate or sugar-based food without jeopardizing the ketogenic state and shifting back into a glucose-based metabolic state. Further, such administration facilitates easier transitioning into a ketogenic state while reducing or eliminating the detrimental effects typically associated with entering ketosis.

In some embodiments, a ketogenic composition additionally includes a therapeutically effective amount of vitamin $D_3$. Vitamin $D_3$ is believed to work in conjunction with magnesium and calcium to promote good bone health and to prevent undesirable calcification of soft tissues. In preferred embodiments, vitamin $D_3$ is included in an amount such that an average daily dose of the ketogenic composition includes about 200 IU ("International Units") to about 8000 IU, or about 400 IU to about 4000 IU, or about 600 IU to about 3000 IU of vitamin $D_3$. In some embodiments, vitamin $D_3$ is included in an amount such that an average daily dose of the ketogenic composition includes about 5 μg to about 200 μg, or about 10 μg to about 100 μg, or about 15 μg to about 75 μg of vitamin $D_3$.

Some embodiments also include one or more additional ketone precursors or supplements. These additional ketone precursors or supplements might include acetoacetate, ketone esters, and/or other compounds that cause a rise in blood ketone levels without adding more electrolytes to the bloodstream. Other additives include metabolites that enhance the effect or transport of ketone bodies into mitochondria, caffeine, theobromine, and nootropics, such as L-alpha glycerylphosphorylcholine ("alpha GPC").

The composition may include flavoring agents that help mask the taste of beta-hydroxybutyrate compounds. These include essential oils, such as peppermint, natural and artificial sweeteners, and other flavorants known in the art.

In some embodiments, ketogenic compositions may further include one or more additional components configured to lower the hygroscopicity of the composition. For example, various anticaking agents, flow agents, and/or moisture absorbers, in types and amounts that are safe for consumption, may be included. Such additional components may include one or more of an aluminosilicate, ferrocyanide, carbonate or bicarbonate salt, silicate (e.g., sodium or calcium silicate), silica, phosphate salt (e.g., di- or tricalcium phosphate), talc, powdered cellulose, calcium carbonate, and the like.

III. Administration

In some embodiments, the compositions disclosed herein can be used in a method for increasing ketone body level, including promoting and/or sustaining ketosis, in a subject comprising administering to a subject in need thereof a nutritionally or pharmaceutically effective amount of one or more compositions disclosed herein. Examples of beneficial effects of increasing ketone body level, including promoting and/or sustaining ketosis, in a subject include one or more of appetite suppression, weight loss, fat loss, reduced blood glucose level, improved mental alertness, increased physical energy, improved cognitive function, reduction in traumatic brain injury, reduction in effect of diabetes, improvement of neurological disorder, reduction of cancer, reduction of inflammation, anti-aging, antiglycation, reduction in epileptic seizer, improved mood, increased strength, increased muscle mass, or improved body composition.

Ketogenic compositions described herein may be administered to a subject in therapeutically effective dosages and/or in frequencies to induce or sustain ketosis. In some embodiments, a single (or unit) dose will include an amount of R-beta-hydroxybutyrate mixed salt-acid compositions ranging from about 0.5 gram to about 25 grams, or about 0.75 gram to about 20 grams, or about 1 gram to about 15 grams, or about 1.5 grams to about 12 grams.

The term "unit dose" refers to a dosage form that is configured to deliver a specified quantity or dose of composition or component thereof. Example dosage forms include, but are not limited to, tablets, capsules, powders, food products, food additives, beverages (such as flavored, vitamin fortified, or non-alcoholic), beverage additives (such as flavored, vitamin fortified, or non-alcoholic), candies, suckers, pastilles, food supplements, dietetically acceptable sprays (such as flavored mouth spray), injectables (such as an alcohol-free injectable), and suppositories. Such dosage forms may be configured to provide a full unit dose or fraction thereof (e.g., ½, ⅓, or ¼ of a unit dose).

Another dosage form that can be used to provide a unit dose of composition or component thereof is a unit dose measuring device, such as a cup, scoop, syringe, dropper, spoon, spatula, or colonic irrigation device, which is configured to hold therein a measured quantity of composition equaling a full unit dose or fraction thereof (e.g., ½, ⅓, or ¼ of a unit dose). For example, a bulk container, such as a carton, box, can, jar, bag, pouch, bottle, jug, or keg, containing several unit doses of composition (e.g., 5-250 or 10-150 unit doses) can be provided to a user together with a unit dose measuring device that is configured to provide a unit dose, or fraction thereof, of composition or component thereof.

A kit for use in providing a composition as disclosed herein in bulk form, while providing unit doses of the composition, may comprise a bulk container holding therein a quantity of composition and a unit dose measuring device configured to provide a unit dose, or fraction thereof, of composition or component thereof. One or more unit dose measuring devices may be positioned inside the bulk container at the time of sale, attached to the outside of the bulk container, prepackaged with the bulk container within a larger package, or provided by the seller or manufacture for use with one or multiple bulk containers.

The kit may include instructions regarding the size of the unit dose, or fraction thereof, and the manner and frequency of administration. The instructions may be provided on the bulk container, prepackaged with the bulk container, placed on packaging material sold with the bulk container, or otherwise provided by the seller or manufacturer (e.g., on websites, mailers, flyers, product literature, etc.) The instructions for use may include a reference on how to use the unit dose measuring device to properly deliver a unit dose or fraction thereof. The instructions may additionally or alternatively include a reference to common unit dose measuring devices, such as spoons, spatulas, cups, and the like, not provided with the bulk container (e.g., in case the provided unit dose measuring device is lost or misplaced). In such case, a kit may be constructed by the end user when following instructions provided on or with the bulk container, or otherwise provided by the seller regarding the product and how to properly deliver a unit dose of composition, or fraction thereof.

In some embodiments, the ketogenic compositions can include or be administered together with other supplements, such as vitamin $D_3$, vitamins, minerals, nootropics, and others known in the art. Examples of vitamins, minerals and herbal supplements that can be added to the ketogenic compositions include one or more of vitamin A, vitamin C, vitamin E, niacin, vitamin B6, folic acid, 5-MTHF, vitamin B12, iodine, zinc, copper, manganese, chromium, caffeine, theobromine, theacrine, methylliberine, huperzine A, epicatechins, and enzymes.

In some embodiments, the subject preferably follows a ketogenic diet that restricts intake of carbohydrates and protein during the period of administration of the composition. In one example embodiment, the subject may restrict the dietary intake to a ratio of about 65% fat, about 25% protein, and about 10% carbohydrates. The resulting therapeutic ketosis provides a rapid and sustained keto-adaptation as a metabolic therapy for a wide range of metabolic disorders, and provides nutritional support for therapeutic fasting, weight loss, and performance enhancement. As such, the composition is typically administered once per day, twice per day, or three times per day to a subject desiring to promote and/or sustain a state of ketosis.

In some embodiments, ketogenic compositions can be administered in one or more unit doses per day via oral administration in solid and/or powdered form, such as in a powdered mixture (e.g., powder filled gelatin capsules), hard-pressed tablets, or other oral administration route known to those skilled in the art.

In some embodiments, multiple doses of the composition are administered over a period of time. The frequency of administration of the composition can vary depending on any of a variety of factors, such as timing of treatment from previous treatments, objectives of the treatment, and the like. The duration of administration of the composition (e.g., the period of time over which the agent is administered), can vary depending on any of a variety of factors, including subject response, desired effect of treatment, etc.

The amount of the composition to be administered can vary according to factors such as the degree of susceptibility of the individual, the age, sex, and weight of the individual, idiosyncratic responses of the individual, and the like. The "therapeutically effective amount" is that amount necessary to promote a therapeutically effective result in vivo (i.e., therapeutic ketosis). In accordance with the present disclosure, a suitable single dose size is a dose that is capable of preventing or alleviating (reducing or eliminating) a symptom in a patient when administered one or more times over a suitable time period.

The amount of composition administered will depend on potency, absorption, distribution, metabolism, and excretion rates of unused ketone bodies, electrolytes, the method of administration, and the particular disorder being treated, as well as other factors known to those of skill in the art. The dose should be sufficient to affect a desirable response, such as a therapeutic or prophylactic response against a particular disorder or condition, taking into account the severity of the condition to be alleviated. The compounds may be administered once, or may be divided and administered over intervals of time. It is to be understood that administration may be adjusted according to individual need and professional judgment of a person administrating or supervising the administration of the compositions.

IV. Examples

The following is a description of exemplary R-beta-hydroxybutyrate mixed salt-acid compositions useful for raising ketone levels in a subject, including inducing and/or modulating a ketogenic state in a subject to which they are administered. The compositions can include a blend of R-beta-hydroxybutyrate salts and the free R-beta-hydroxybutyric acid, to provide a desired electrolyte balance, taste and/or pharmacokinetic response. The compositions can also be combined with short, medium, or long chain fatty acids, esters, glycerides, and other supplements as disclosed herein to provide a desired level of elevated ketone bodies and other effects.

Example 1

A R-beta-hydroxybutyrate mixed salt-acid composition is prepared by combining one or more enantiomerically pure R-beta-hydroxybutyrate salts with enantiomerically pure R-beta-hydroxybutyric acid so as to provide 99% by molar equivalents of R-beta-hydroxybutyrate salt(s) and 1% by molar equivalents of R-beta-hydroxybutyric acid. Because the composition includes a relatively small quantity of R-beta-hydroxybutyric acid compared to R-beta-hydroxybutyrate salt(s), the composition is absorbed only slightly (yet significantly) faster than a composition containing only salt forms of BHB but substantially faster than ester forms of R-beta-hydroxybutyrate.

The R-beta-hydroxybutyrate mixed salt-acid composition is administered as a ketogenic composition, such as in powder form as a dietary supplement mixed with food or drink, in the form of one or more capsules or tablets, or in liquid form such as a mouth spray.

Example 2

A R-beta-hydroxybutyrate mixed salt-acid composition is prepared by combining one or more enantiomerically pure R-beta-hydroxybutyrate salts with enantiomerically pure R-beta-hydroxybutyric acid so as to provide 98% by molar equivalents of R-beta-hydroxybutyrate salt(s) and 2% by molar equivalents of R-beta-hydroxybutyric acid. Because the composition includes a higher percentage of R-beta-hydroxybutyric acid compared to Example 1, the composition is absorbed faster than the composition of Example 1. On the other hand, the inclusion of a substantial percentage of R-beta-hydroxybutyrate salt(s) still provides a delay in absorption that can provide for a relative slow increase in blood ketone body level in a subject as compared to compositions containing higher amounts of R-beta-hydroxybutyric acid.

Example 3

A R-beta-hydroxybutyrate mixed salt-acid composition is prepared by combining one or more enantiomerically pure R-beta-hydroxybutyrate salts with enantiomerically pure R-beta-hydroxybutyric acid so as to provide 97% by molar equivalents of R-beta-hydroxybutyrate salt(s) and 3% by molar equivalents of R-beta-hydroxybutyric acid. Because the composition includes a higher percentage of R-beta-hydroxybutyric acid compared to Examples 1 and 2, the composition is absorbed faster than the compositions of Examples 1 and 2. On the other hand, the inclusion of a substantial percentage of R-beta-hydroxybutyrate salt(s) still provides a delay in absorption that can provide for a relative slow increase in blood ketone body level in a subject as compared to compositions containing higher amounts of R-beta-hydroxybutyric acid.

Example 4

A R-beta-hydroxybutyrate mixed salt-acid composition is prepared by combining one or more enantiomerically pure R-beta-hydroxybutyrate salts with enantiomerically pure R-beta-hydroxybutyric acid so as to provide 96% by molar equivalents of R-beta-hydroxybutyrate salt(s) and 4% by molar equivalents of R-beta-hydroxybutyric acid. Because the composition includes a higher percentage of R-beta-hydroxybutyric acid compared to Examples 1-3, the composition is absorbed faster than the compositions of Examples 1-3. On the other hand, the inclusion of a substantial percentage of R-beta-hydroxybutyrate salt(s) still provides some delay in absorption that can provide for slower increase in blood ketone body level in a subject as compared to compositions containing higher amounts of R-beta-hydroxybutyric acid.

Example 5

A R-beta-hydroxybutyrate mixed salt-acid composition is prepared by combining one or more enantiomerically pure R-beta-hydroxybutyrate salts with enantiomerically pure R-beta-hydroxybutyric acid so as to provide 95% by molar equivalents of R-beta-hydroxybutyrate salt(s) and 5% by molar equivalents of R-beta-hydroxybutyric acid. Because the composition includes a higher percentage of R-beta-hydroxybutyric acid compared to Examples 1-4, the composition is absorbed faster than the compositions of Examples 1-4. On the other hand, the inclusion of a substantial percentage of R-beta-hydroxybutyrate salt(s) still provides some delay in absorption that can provide for slower increase in blood ketone body level in a subject as compared to compositions containing higher amounts of R-beta-hydroxybutyric acid.

Example 6

A R-beta-hydroxybutyrate mixed salt-acid composition is prepared by combining one or more enantiomerically pure R-beta-hydroxybutyrate salts with enantiomerically pure R-beta-hydroxybutyric acid so as to provide 94% by molar equivalents of R-beta-hydroxybutyrate salt(s) and 6% by molar equivalents of R-beta-hydroxybutyric acid. Because the composition includes a higher percentage of R-beta-hydroxybutyric acid compared to Examples 1-5, the composition is absorbed faster than the compositions of Examples 1-5. On the other hand, the inclusion of a substantial percentage of R-beta-hydroxybutyrate salt(s) still provides some delay in absorption that can provide for slower increase in blood ketone body level in a subject as compared to compositions containing higher amounts of R-beta-hydroxybutyric acid.

Example 7

A R-beta-hydroxybutyrate mixed salt-acid composition is prepared by combining one or more enantiomerically pure R-beta-hydroxybutyrate salts with enantiomerically pure R-beta-hydroxybutyric acid so as to provide 92% by molar equivalents of R-beta-hydroxybutyrate salt(s) and 8% by molar equivalents of R-beta-hydroxybutyric acid. Because the composition includes a higher percentage of R-beta-hydroxybutyric acid compared to Examples 1-6, the composition is absorbed faster than the compositions of Examples 1-6. On the other hand, the inclusion of a major percentage of R-beta-hydroxybutyrate salt(s) still provides some delay in absorption that can provide for slower increase in blood ketone body level in a subject as compared to compositions containing higher amounts of R-beta-hydroxybutyric acid.

Example 8

A R-beta-hydroxybutyrate mixed salt-acid composition is prepared by combining one or more enantiomerically pure R-beta-hydroxybutyrate salts with enantiomerically pure R-beta-hydroxybutyric acid so as to provide 90% by molar equivalents of R-beta-hydroxybutyrate salt(s) and 10% by molar equivalents of R-beta-hydroxybutyric acid. Because the composition includes a higher percentage of R-beta-hydroxybutyric acid compared to Examples 1-7, the composition is absorbed faster than the compositions of Examples 1-7. On the other hand, the inclusion of a major percentage of R-beta-hydroxybutyrate salt(s) still provides some delay in absorption that can provide for slower increase in blood ketone body level in a subject as compared to compositions containing higher amounts of R-beta-hydroxybutyric acid.

Example 9

A R-beta-hydroxybutyrate mixed salt-acid composition is prepared by combining one or more enantiomerically pure R-beta-hydroxybutyrate salts with enantiomerically pure R-beta-hydroxybutyric acid so as to provide 85% by molar equivalents of R-beta-hydroxybutyrate salt(s) and 15% by molar equivalents of R-beta-hydroxybutyric acid. Because the composition includes a higher percentage of R-beta-hydroxybutyric acid compared to Examples 1-8, the composition is absorbed faster than the compositions of Examples 1-8. On the other hand, the inclusion of a major percentage of R-beta-hydroxybutyrate salt(s) still provides some delay in absorption that can provide for slower increase in blood ketone body level in a subject as compared to compositions containing higher amounts of R-beta-hydroxybutyric acid.

Example 10

A R-beta-hydroxybutyrate mixed salt-acid composition is prepared by combining one or more enantiomerically pure R-beta-hydroxybutyrate salts with enantiomerically pure R-beta-hydroxybutyric acid so as to provide 80% by molar equivalents of R-beta-hydroxybutyrate salt(s) and 20% by molar equivalents of R-beta-hydroxybutyric acid. Because the composition includes a higher percentage of R-beta-hydroxybutyric acid compared to Examples 1-9, the composition is absorbed faster than the compositions of Examples 1-9. On the other hand, the inclusion of a major percentage of R-beta-hydroxybutyrate salt(s) still provides some delay in absorption that can provide for slower increase in blood ketone body level in a subject as compared to compositions containing higher amounts of R-beta-hydroxybutyric acid.

Example 11

A R-beta-hydroxybutyrate mixed salt-acid composition is prepared by combining one or more enantiomerically pure R-beta-hydroxybutyrate salts with enantiomerically pure R-beta-hydroxybutyric acid so as to provide 75% by molar equivalents of R-beta-hydroxybutyrate salt(s) and 25% by molar equivalents of R-beta-hydroxybutyric acid. Because the composition includes a higher percentage of R-beta-hydroxybutyric acid compared to Examples 1-10, the composition is absorbed faster than the compositions of Examples 1-10. On the other hand, the inclusion of a major percentage of R-beta-hydroxybutyrate salt(s) still provides some delay in absorption that can provide for slower increase in blood ketone body level in a subject as compared to compositions containing higher amounts of R-beta-hydroxybutyric acid.

Example 12

Any of the foregoing R-beta-hydroxybutyrate mixed salt-acid compositions of Examples 1-11, or variation thereof, is mixed with a dietetically (i.e., nutritionally) or pharmaceutically acceptable carrier.

Example 13

Any of the foregoing examples is modified by combining the R-beta-hydroxybutyrate mixed salt-acid composition with one or more short chain fatty acids, and/or one or more mono-, di- or triglycerides thereof, such as tributyrin.

Example 14

Any of the foregoing examples is modified by combining the R-beta-hydroxybutyrate mixed salt-acid composition with one or more medium chain fatty acids, and/or one or more mono-, di- or triglycerides thereof, such as MCT oil.

Example 15

Any of the foregoing examples is modified by combining the R-beta-hydroxybutyrate mixed salt-acid composition with one or more long chain fatty acids, and/or one or more mono-, di- or triglycerides thereof.

Example 16

Any of the foregoing examples is modified by combining the R-beta-hydroxybutyrate mixed salt-acid composition with one or more supplements, such as vitamin $D_3$, vitamins, minerals, and others known in the art.

Example 17

Any of the foregoing examples is modified by combining the R-beta-hydroxybutyrate mixed salt-acid composition with one or more additives or metabolites that enhance the effect or transport of ketone bodies into mitochondria, caffeine, theobromine, or nootropic, such as L-alpha glycerylphosphorylcholine.

Example 18

A R-beta-hydroxybutyrate mixed salt-acid composition is manufactured so as to contain up to 99.9%, 99.8%, 99.7%, 99.6%, 99.5%, 99.4%, 99.3%, 99.2%, 99.1%, 99%, 98.8%, 98.65%, 98.5%, 98.35%, 98.2%, 98%, 97.75%, 97.5%, 97.25%, or 97% of one or more enantiomerically pure R-beta-hydroxybutyrate salts, and at least 0.1%, 0.2%, 0.3%, 0.4%, 0.5%, 0.6%, 0.7%, 0.8%, 0.9%, 1%, 1.2%, 1.35%, 1.5%, 1.65%, 1.8%, 2%, 2.25%, 2.5%, 2.75%, or 3%, of free enantiomerically pure R-beta-hydroxybutyric acid.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. An R-beta-hydroxybutyrate mixed salt-acid composition for increasing ketone level in a subject, comprising:
   enantiomerically pure R-beta-hydroxybutyric acid; and
   one or more enantiomerically pure R-beta-hydroxybutyrate salts comprising at least enantiomerically pure magnesium R-beta-hydroxybutyrate;
   wherein the mixed salt-acid composition comprises 75% to 99.9% by molar equivalents of total enantiomerically pure R-beta-hydroxybutyrate salts and 25% to 0.1% by molar equivalents of the enantiomerically pure R-beta-hydroxybutyric acid and is in solid and/or powder form.

2. The R-beta-hydroxybutyrate mixed salt-acid composition of claim 1, further comprising at least one of:
   enantiomerically pure sodium R-beta-hydroxybutyrate;
   enantiomerically pure potassium R-beta-hydroxybutyrate; or
   enantiomerically pure calcium R-beta-hydroxybutyrate.

3. The R-beta-hydroxybutyrate mixed salt-acid composition of claim 1, further comprising at least two of:
   enantiomerically pure sodium R-beta-hydroxybutyrate;
   enantiomerically pure potassium R-beta-hydroxybutyrate; or
   enantiomerically pure calcium R-beta-hydroxybutyrate.

4. The R-beta-hydroxybutyrate mixed salt-acid composition of claim 1, wherein the composition comprises:
   enantiomerically pure sodium R-beta-hydroxybutyrate;
   enantiomerically pure potassium R-beta-hydroxybutyrate;
   enantiomerically pure calcium R-beta-hydroxybutyrate; and
   enantiomerically pure magnesium R-beta-hydroxybutyrate.

5. The R-beta-hydroxybutyrate mixed salt-acid composition of claim 1, wherein the mixed salt-acid composition comprises 80% to 99.7% by molar equivalents of total enantiomerically pure R-beta-hydroxybutyrate salts and 20% to 0.3% by molar equivalents of the enantiomerically pure R-beta-hydroxybutyric acid.

6. The R-beta-hydroxybutyrate mixed salt-acid composition of claim 1, wherein the mixed salt-acid composition comprises 85% to 99.5% by molar equivalents of total enantiomerically pure R-beta-hydroxybutyrate salts and 15% to 0.5% by molar equivalents of the enantiomerically pure R-beta-hydroxybutyric acid.

7. The R-beta-hydroxybutyrate mixed salt-acid composition of claim 1, wherein the mixed salt-acid composition comprises 90% to 99% by molar equivalents of total enantiomerically pure R-beta-hydroxybutyrate salts and 10% to 1% by molar equivalents of the enantiomerically pure R-beta-hydroxybutyric acid.

8. The R-beta-hydroxybutyrate mixed salt-acid composition of claim 1, further comprising at least one short chain fatty acid having less than 6 carbons, or a mono-, di- or triglyceride of the at least one short chain fatty acid.

9. The R-beta-hydroxybutyrate mixed salt-acid composition of claim 1, further comprising at least one medium chain fatty acid having 6 to 12 carbons, or a mono-, di- or triglyceride of the at least one medium chain fatty acid.

10. The R-beta-hydroxybutyrate mixed salt-acid composition of claim 1, further comprising a R-beta-hydroxybutyrate salt having a cation selected from the group consisting of other alkali metals, other alkaline earth metals, transition metals, amino acids, or metabolites of amino acids.

11. The R-beta-hydroxybutyrate mixed salt-acid composition of claim 10, wherein the R-beta-hydroxybutyrate salt is selected from the group consisting of lithium salts, zinc salts, iron salts, chromium salts, manganese salts, cobalt salts, copper salts, molybdenum salts, selenium salts, arginine salts, lysine salts, leucine salts, isoleucine salts, histidine salts, ornithine salts, citrulline salts, glutamine salts, and creatine salts.

12. The R-beta-hydroxybutyrate mixed salt-acid composition of claim 1, further comprising at least one supplement selected from vitamin, mineral, nootropic, and herbal supplement.

13. An R-beta-hydroxybutyrate mixed salt-acid composition for increasing ketone level in a subject, comprising:
   enantiomerically pure R-beta-hydroxybutyric acid; and
   one or more enantiomerically pure R-beta-hydroxybutyrate salts selected from:
      enantiomerically pure sodium R-beta-hydroxybutyrate;
      enantiomerically pure potassium R-beta-hydroxybutyrate;
      enantiomerically pure calcium R-beta-hydroxybutyrate; and
      enantiomerically pure magnesium R-beta-hydroxybutyrate,
   wherein the mixed salt-acid composition comprises 75% to 99.5% by molar equivalents of total enantiomerically pure R-beta-hydroxybutyrate salts and 25% to 0.5% by molar equivalents of the enantiomerically pure R-beta-hydroxybutyric acid and is provided as or in a tablet, capsule, powder, food product, food additive, flavored beverage, vitamin fortified beverage, non-alcoholic beverage, flavored beverage additive, vitamin fortified beverage additive, non-alcoholic beverage additive, candy, sucker, pastille, food supplement, flavored mouth spray, or suppository.

14. The R-beta-hydroxybutyrate mixed salt-acid composition of claim 13, wherein the composition comprises 80% to 99% by molar equivalents of total enantiomerically pure R-beta-hydroxybutyrate salts and 20% to 1% by molar equivalents of the enantiomerically pure R-beta-hydroxybutyric acid.

15. An R-beta-hydroxybutyrate mixed salt-acid composition for increasing ketone level in a subject, comprising:
   a dietetically or pharmaceutically acceptable carrier selected from the group consisting of tablet, capsule, powder, food product, food additive, flavored beverage, vitamin fortified beverage, non-alcoholic beverage, flavored beverage additive, vitamin fortified beverage additive, non-alcoholic beverage additive, candy, sucker, pastille, food supplement, flavored mouth spray, and suppository;

enantiomerically pure R-beta-hydroxybutyric acid; and one or more enantiomerically pure R-beta-hydroxybutyrate salts selected from:

enantiomerically pure sodium R-beta-hydroxybutyrate;

enantiomerically pure potassium R-beta-hydroxybutyrate;

enantiomerically pure calcium R-beta-hydroxybutyrate; and enantiomerically pure magnesium R-beta-hydroxybutyrate wherein the composition comprises 75% to 99.9% by molar equivalents of total enantiomerically pure R-beta-hydroxybutyrate salts and 25% to 0.1% by molar equivalents of the enantiomerically pure R-beta-hydroxybutyric acid.

16. The R-beta-hydroxybutyrate mixed salt-acid composition of claim 15, wherein the composition comprises 80% to 99.8% by molar equivalents of total enantiomerically pure R-beta-hydroxybutyrate salts and 20% to 0.2% by molar equivalents of the enantiomerically pure R-beta-hydroxybutyric acid.

17. A kit for administering ketone bodies to a subject, comprising:

an R-beta-hydroxybutyrate mixed salt-acid composition in powder form comprising:

enantiomerically pure R-beta-hydroxybutyric acid; and one or more enantiomerically pure R-beta-hydroxybutyrate salts selected from:

enantiomerically pure sodium R-beta-hydroxybutyrate;

enantiomerically pure potassium R-beta-hydroxybutyrate;

enantiomerically pure calcium R-beta-hydroxybutyrate; and enantiomerically pure magnesium R-beta-hydroxybutyrate, wherein the mixed salt-acid composition comprises 75% to 99.9% by molar equivalents of total enantiomerically pure R-beta-hydroxybutyrate salts and 25% to 0.1% by molar equivalents of the enantiomerically pure R-beta-hydroxybutyric acid;

a container in which the R-beta-hydroxybutyrate mixed-salt composition is placed; and a measuring device configured to hold therein a unit dose, or fraction thereof, of the R-beta-hydroxybutyrate mixed-salt composition, wherein a unit dose of the composition contains about 0.5 g to about 25 g of R-beta-hydroxybutyrate compounds.

18. The kit of claim 17, wherein the container is selected from the group consisting of carton, box, can, jar, bag, pouch, bottle, jug, and keg.

19. The kit of claim 17 or 18, wherein the measuring device is selected from the group consisting of cup, scoop, syringe, dropper, spatula, spoon, and colonic irrigation device.

20. The kit of claim 17, wherein the composition comprises 75% to 99.7% by molar equivalents of total enantiomerically pure R-beta-hydroxybutyrate salts and 25% to 0.3% by molar equivalents of the enantiomerically pure R-beta-hydroxybutyric acid.

\* \* \* \* \*

UNITED STATES PATENT AND TRADEMARK OFFICE
CERTIFICATE OF CORRECTION

PATENT NO. : 11,241,401 B2
APPLICATION NO. : 16/783907
DATED : February 8, 2022
INVENTOR(S) : Gary Millet It is certified that error appears in the above-identified patent and that said Letters Patent is hereby corrected as shown below:

In the Specification

Column 3
Line 66, change "compounds" to – compound –

Column 3
Line 67, change "compounds" to – compound –

Signed and Sealed this
Nineteenth Day of July, 2022

Katherine Kelly Vidal
*Director of the United States Patent and Trademark Office*